United States Patent [19]
Ramaswamy et al.

[11] Patent Number: 5,965,734
[45] Date of Patent: Oct. 12, 1999

[54] PROCESSES AND INTERMEDIATES FOR PREPARING 2-SUBSTITUTED PIPERIDINE STEREOISOMERS

[75] Inventors: Sowmianarayanan Ramaswamy, Bridgewater; Vikram Khetani, Jersey City, both of N.J.

[73] Assignee: Celgene Corporation, Warren, N.J.

[21] Appl. No.: 08/792,661

[22] Filed: Jan. 31, 1997

[51] Int. Cl.$^6$ .................................................. C07D 211/32
[52] U.S. Cl. ............................................................ 546/233
[58] Field of Search ............................................. 546/233

[56] References Cited

U.S. PATENT DOCUMENTS

| | | | |
|---|---|---|---|
| 2,507,631 | 5/1950 | Hartmann et al. | 546/233 |
| 2,957,880 | 10/1960 | Rometsch | 546/233 |
| 4,395,558 | 7/1983 | Kasai et al. | 548/422 |
| 4,978,744 | 12/1990 | Pettit et al. | 530/330 |
| 5,075,315 | 12/1991 | Rasmussen | 514/266 |

OTHER PUBLICATIONS

Jaric et al, Chemical Abstract vol. 122 No. 12242, "Ret Openationium Aong Phenyolacteoids" 1994.
Patrick et al, Chemical Abstract vol. 97 No. 144733 "Syn of Deuterium Methylphenidate" 1982.
Soares, "Stereiochemical Studies on Potentail Central Nervous System Active Agents and Studies on the Chemistry of Some 3–Benzoylpiperidines", Columbia University Ph.D. dissertation, 1971, p. 115.

*Primary Examiner*—John Kight
*Assistant Examiner*—Raymond Covington
*Attorney, Agent, or Firm*—Woodcock Wasburn Kurtz Mackiewicz & Norris, LLP

[57] ABSTRACT

Processes and intermediates for preparing 2-substituted piperidines such as 2-substituted d-threo piperidines are provided. In preferred embodiments, the processes of the invention comprise the steps of reacting a 2-substituted pyridine with hydrogen in the presence of a catalyst in an alkanoic acid, and adding an alkyl alkanoate to the resulting mixture of threo and erythro 2-piperidine stereoisomers to precipitate alkanoate salts of the erythro stereoisomers preferentially with respect to alkanoate salts of the threo stereoisomers. The erythro salts then are reacted with aqueous base to form the corresponding mixture of erythro amide free bases, which are reacted with a suitable organic acid resolving agent in an alkyl alcohol solvent to form acid salts of the l-erythro stereoisomers preferentially with respect to the d-erythro stereoisomers. The l-erythro acid salts are then reacted with aqueous base to form the l-erythro piperidine amide free base which, in turn, is epimerized to produce the desired d-threo product by treating it in an organic solvent with an alkali metal alkoxide.

23 Claims, No Drawings

PROCESSES AND INTERMEDIATES FOR PREPARING 2-SUBSTITUTED PIPERIDINE STEREOISOMERS

FIELD OF THE INVENTION

This invention is directed to novel processes for stereoselective preparation of 2-substituted piperidines. The invention additionally is directed to novel synthetic intermediates and reaction products useful in such processes.

BACKGROUND OF THE INVENTION

Substituted piperidines have found use in the treatment of many nervous system disorders. For example, methylphenidate has been used to treat Attention Deficit Disorder (ADD), Attention Deficit Hyperactivity Disorder (ADHD) and cognitive decline in Acquired Immunodeficiency Syndrome (AIDS) and AIDS Related Complex (ARC) patients. (See, e.g., Greenhill, *Child & Adol. Psych. Clin. N.A.*, 1995, 4, 123, and Brown, *Intl. J. Psychl. Med.*, 1995, 25, 21).

Many currently available synthetic routes to methylphenidate and other substituted piperidines involve preparation of racemic mixtures. (See, e.g., U.S. Pat. No. 2,507,631, to Hartmann, et al., and U.S. Pat. No. 2,957,880, to Rometsch, et al.). There are, however, a number of disadvantages associated with racemic mixtures of such drugs. Current administration of racemic methylphenidate often results in notable side effects such as anorexia, weight loss, insomnia, dizziness and dysphoria. Additionally, racemic methylphenidate produces a euphoric effect when administered intravenously or through inhalation, and thus carries a high potential for substance abuse in patients.

U.S. Pat. Nos. 2,507,631 and 2,957,880 disclose synthetic procedures wherein methylphenidate, alternatively known as methyl α-piperid-2-ylphenylacetate, is prepared through a multi-step process in which 2-chloropyridine and phenylacetonitrile initially are coupled to form α-pyrid-2-ylphenylacetonitrile. The resulting α-pyrid-2-ylphenylacetonitrile then is hydrated in the presence of acid to yield α-pyrid-2-ylphenylacetamide which, in turn, is either: (a) catalytically hydrogenated to yield α-piperid-2-ylphenylacetamide and then converted to methyl α-piperid-2-ylphenylacetate, or (b) converted to methyl α-pyrid-2-ylphenylacetate which, in turn, is hydrogenated to yield methyl α-piperid-2-ylphenylacetate.

In the first embodiment of U.S. Pat. No. 2,507,631 and in the process described in U.S. Pat. No. 2,957,880, α-piperid-2-ylphenylacetamide is first separated into the threo and erythro diastereomeric racemates. This is accomplished through evaporation of the solvent utilized in the hydrogenation (i.e., acetic acid), addition of sodium hydroxide to precipitate the α-piperid-2-ylphenylacetamide free base, recrystallization of this amide from ethyl acetate, and preferential crystallization of the erythro form by passing gaseous hydrogen chloride through an ethanolic solution of the amide. The isolated erythro racemate then is resolved through formation of the l-tartrate salt, repeated recrystallizations of this salt from 96% ethanol are performed until a constant rotation is obtained, and the l-erythro form of α-piperid-2-ylphenylacetamide is precipitated with sodium hydroxide. The l-erythro form of α-piperid-2-ylphenylacetamide thus obtained is said to be subjected to epimerization to yield the desired d-threo diastereomer of α-piperid-2-ylphenylacetamide through treatment with 6 M potassium hydroxide. According to the disclosed procedure, the α-piperid-2-ylphenylacetamide thus obtained is converted to d-threo methyl α-piperid-2-ylphenylacetate through hydrolysis and esterification.

Some in the art have raised doubts as to whether the procedures disclosed in U.S. Pat. Nos. 2,507,631 and 2,957,880 do, in fact, produce the desired d-threo isomer. Indeed, J. R. Scares, "Stereochemical Studies On Potential Central Nervous System Active Agents and Studies On The Chemistry Of Some 3-Benzoylpiperidines," 1971, Columbia University Ph.D. dissertation, p. 115, discloses that "all attempts to epimerize the resolved erythro-amides to the corresponding threo-amides by the procedure outlined in [U.S. Pat. No. 2,957,880] failed completely."

Consequently, there remains a need in the art for alternative synthetic procedures for the preparation of methylphenidate and other substituted piperidines.

OBJECTS OF THE INVENTION

It is an object of the present invention to provide processes for preparation of substituted piperidines.

It is another object of this invention to provide processes that provide products having high optical purity.

It is yet another object to provide processes that proceed more efficiently than the processes disclosed by the prior art.

SUMMARY OF THE INVENTION

These and other objects are satisfied by the present invention, which provides processes and intermediates for preparing 2-substituted piperidine stereoisomers such as 2-substituted d-threo piperidines. In certain embodiments, the processes of the invention comprise the steps of reacting a pyridine having formula I:

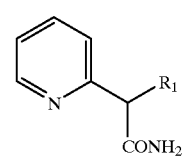

I wherein $R_1$ is aryl having about 6 to about 28 carbon atoms with hydrogen in the presence of a catalyst in an alkanoic acid having 1 to about 10 carbon atoms. This reaction produces a mixture of threo and erythro piperidine stereoisomers having formulas IIa–d:

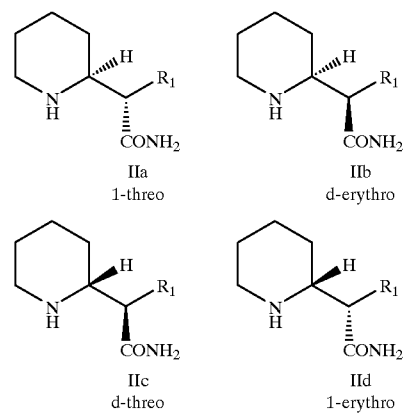

IIa
1-threo

IIb
d-erythro

IIc
d-threo

IId
1-erythro

To this mixture is added an alkyl alkanoate having 2 to about 20 carbon atoms, thereby precipitating alkanoate salts of erythro stereoisomers IIb and IId preferentially with respect to alkanoate salts of threo stereoisomers IIa and IIc.

The erythro salts then are optionally separated from the threo salts and reacted with aqueous base to form the corresponding erythro amide free base. The mixture of erythro amide stereoisomers then is reacted with a suitable organic acid resolving agent in an alkyl alcohol having 1 to about 5 carbon atoms, thereby forming acid salts of the l-erythro stereoisomers preferentially with respect to the d-erythro stereoisomers. The l-erythro acid salts are optionally separated from the d-erythro acid salts and then reacted with aqueous base to form l-erythro piperidine IId. The l-erythro piperidine, in turn, is epimerized to produce the desired d-threo product IIc by treating it in an organic solvent with an alkali metal alkoxide having one to about 10 carbon atoms.

DETAILED DESCRIPTION OF THE INVENTION

This invention provides novel processes for stereoselective synthesis of a variety 2-substituted piperidine stereoisomers. Although preferred processes are those directed to the d-threo stereoisomers, those skilled in the art will recognize that the processes and techniques disclosed herein can be readily adapted to the synthesis of the other stereoisomer, as well. All such synthetic processes are within the scope of the present invention.

In one aspect, the present invention is directed to synthetic methods involving hydrogenation of pyridines having formula I:

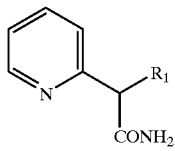

I wherein $R_1$ is aryl having about 6 to about 28 carbon atoms. This hydrogenation can be effected by any of the numerous techniques known in the art. One preferred hydrogenation technique involves reacting the pyridine with hydrogen gas in the presence of a suitable catalyst in an alkanoic acid having 1 to about 10 carbon atoms. The hydrogenation preferably run at 25° C. and 40 psi. Representative catalysts contain platinum, with platinum oxide being particularly preferred. One preferred alkanoic acid is acetic acid.

Hydrogenation of pyridine I provides a mixture of piperidine diastereomers IIa–d:

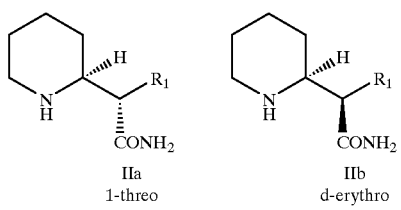

IIa
l-threo

IIb
d-erythro

-continued

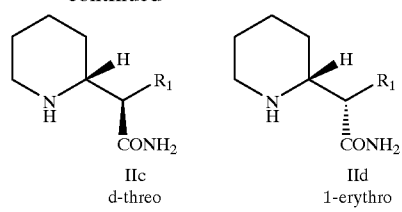

IIc
d-threo

IId
l-erythro

In accordance with the present invention, it surprisingly has been found that the erythro diastereomers can be precipitated from solution preferentially with respect to the threo diastereomers by adding an alkyl alkanoate to the hydrogenation reaction mixture. This precipitation preferably is achieved by allowing the reaction mixture to stand at ambient temperatures. Preferred alkyl alkanoates are those having 2 to about 20 carbon atoms, such as ethyl acetate. Once precipitated, the erythro alkanoate salt can be filtered off, and the mother liquor can be concentrated and further treated with the alkanoate to yield a second crop of crystals. In preferred embodiments, the erythro salt which is collected is dissolved in water and treated with an aqueous base such as a carbonate, bicarbonate, or hydroxide to precipitate the piperidine amide free base in substantially pure (i.e., at least 90 percent pure and, more preferably, at least 99 percent pure) form.

The mixture of erythro amide stereoisomers then is reacted with an acid resolving agent in an alkyl alcohol having 1 to about 5 carbon atoms, thereby forming acid salts of the l-erythro stereoisomers preferentially with respect to the d-erythro stereoisomers. The reaction preferably is performed with stirring at room temperature. Representative resolving agents include L-(+)- or D(−)-tartaric acid, (−)-dibenzoyl-L-tartaric acid, (1S)-(+)-10-camphorsulphonic acid, L-(−)-malic acid, and (S)-(+)-mandelic acid. Representative alcohols include branched and straight chain compounds such as ethyl, propyl and tert-butyl alcohol, with absolute methanol being particularly preferred. The l-erythro acid salt typically is dissolved in water and treated with an aqueous base such as a carbonate, bicarbonate, or hydroxide to precipitate the l-erythro piperidine amide free base in substantially pure form.

The processes of the invention further comprise forming the desired d-threo piperidine product in substantially pure form by epimerizing the l-erythro free base in organic solvent using an alkali metal alkoxide having one to about 10 carbon atoms. In preferred embodiments, the epimerization is effected at 70° C. in an aromatic hydrocarbon solvent such as toluene using two equivalents of an alkali metal alkoxide such as potassium tert-butoxide.

Additional objects, advantages, and novel features of this invention will become apparent to those skilled in the art upon examination of the following examples thereof, which are not intended to be limiting.

EXAMPLE 1

Erythro α-Piperid-2-ylphenylacetamide

A solution of 300 g of α-pyrid-2-ylphenylacetamide in 1.0 L glacial acetic acid was hydrogenated in the presence of 5.0 g of platinum oxide at 40° C. under 40 psi of hydrogen for 24 hours. The reaction mixture was filtered through a 25 g pad of celite and the filtrate concentrated to 750 g and treated with 300 mL of ethyl acetate and allowed to stand overnight at ambient temperature. Crystals of erythro α-piperid-2-ylphenylacetamide acetate were filtered and washed with ethyl acetate and dried under vacuum to give 216 g as the first crop. The mother liquor was concentrated to 400 g and treated with 300 mL of ethyl acetate to give an additional 91 g of product. The combined acetate salt of erythro α-piperid-2-ylphenylacetamide was dissolved in 1.0 L of water, and the pH adjusted to 13. The precipitated free base was washed with deionized water, and the product dried in a vacuum desiccator over solid potassium hydroxide to give 214 g of product which was recrystallized from 4.0 L of ethyl acetate, yielding 175 g of d,l-erythro α-piperid-2-ylphenylacetamide as a white solid.

EXAMPLE 2

Resolution of d,l-Erythro α-Piperid-2-ylphenylacetamide

To a stirred solution of 80 g (0.366 mol) of d,l-erythro α-piperid-2-ylphenylacetamide in 1.92 L of methanol was added a warm solution of 55.0 g (0.366 mol) of D-(−)-tartaric acid in 1.92 L of methanol. The solution was stirred at ambient temperature for 18 hours and the crystals which formed were collected by filtration, washed with cold methanol, and dried under vacuum. The tartrate salt was dissolved in 0.60 L of distilled water, and the pH adjusted to 13. The precipitated free base of the erythro amide was filtered by suction, washed with distilled water, sucked to dryness, and dried under vacuum over potassium hydroxide pellets to yield 26 g of l-erythro α-piperid-2-ylphenylacetamide, $[\alpha]_D$=−59.0°, (60% ethanol/water, c =1.0). Fractional crystallization of 40.0 g of the d-erythro amide enriched product recovered from the mother liquor with L-(+)-tartaric acid afforded 20.7 g of the enantiomeric d-erythro α-piperid-2-ylphenylacetamide, $[\alpha]_D$=+61.0°, (60% ethanol/water, c=1.0).

The foregoing resolution procedure was repeated using 0.5 g samples of d,l-erythro or d,l-threo α-piperid-2-ylphenylacetamide and modifying the resolving agent and/or solvent as indicated below:

Resolution of d,l-erythro α-piperid-2-ylphenylacetamide

| Tartaric Acid (equiv.) | Solvent(s) | Solvent Amt. (per g. amide) | Yield | $[\alpha]_D$ | % ee |
|---|---|---|---|---|---|
| L-(+) (1.0) | 96:4 EtOH:H₂O | 48 mL/g | 124% | +6.5° | 0.0 |
| L-(+) (1.0) | 90:10 EtOH:H₂O | 48 mL/g | 0% | — | — |
| L-(+) (1.0) | 80:20 EtOH:H₂O | 48 mL/g | 0% | — | — |
| L-(+) (1.0) | 70:30 EtOH:H₂O | 48 mL/g | 0% | — | — |
| D-(−) (1.0) | 96:4 EtOH:H₂O | 48 mL/g | 72% | −1.3° | 0.0 |
| D-(−) (1.0) | 100% EtOH | 48 mL/g | 112% | 0° | — |
| D-(−) (1.0) | MeOH | 48 mL/g | 52% | −57.0° | 99.8 |
| D-(−) (1.0) | Isopropanol | 48 mL/g | 76% | 0° | — |
| D-(−) (1.0) | Acetone | 48 mL/g | 88% | 0° | — |
| D-(−) (.25) | 96:4 EtOH:H₂O | 48 mL/g | 52% | 0° | — |
| D-(−) (.50) | 96:4 EtOH:H₂O | 48 mL/g | 112% | 0° | — |
| D-(−) (.75) | 96:4 EtOH:H₂O | 48 mL/g | 80% | −31.9° | 40.2 |
| *D-(−) (1.0) | MeOH | 48 mL/g (100%) | 65.6% | −59.0° | 99.8 |
| **D-(−) (1.0) | MeOH | 48 mL/g (50% less) | 24% | −61.8° | 99.8 |
| **D-(−) (1.0) | MeOH | 24 mL/g | 60% | −30.2° | 34.7 |
| D-(−) (1.0) | MeOH | 36 mL/g (50% less) | 73% | −21.7° | 11.7 |
| D-(−) (1.0) | MeOH | 24 mL/g (25% less) | 84% | −11.3° | ~3 |
| D-(−) (.75) | MeOH | 24 mL/g (50% less) | 40% | −46.0° | 66.2 |
| D-(−) (.75) | MeOH | 48 mL/g (100%) | 48% | −56.6° | 99.8 |
| D-(−) (.75) | MeOH | 36 mL/g (25% less) | 72% | −36.3° | 28.7 |

Resolution of d,l-threo α-piperid-2-ylphenylacetamide

| Tartaric Acid (equiv.) | Solvent(s) | Solvent Amt. (per g. amide) | Yield | $[\alpha]_D$ - 0.3° | % ee |
|---|---|---|---|---|---|
| L-(+) (1.0) | 96:4 EtOH:H₂O | 48 mL/g | 136% | 0° | 0.0 |
| D-(−) (1.0) | 96:4 EtOH:H₂O | 48 mL/g | 148% | 0° | 0.0 |
| D-(−) (1.0) | 100% EtOH | 48 mL/g | 145% | 0° | 0.0 |
| D-(−) (1.0) | 96:4 MeOH:H₂O | 48 mL/g | 84% | −2.3° | 0.0 |
| L-(+) (1.0) | 90:10 MeOH:H₂O | 48 mL/g | 32% | −1.4° | 0.0 |
| L-(+) (1.0) | 80:20 MeOH:H₂O | 48 mL/g | 0% | — | — |
| L-(+) (1.0) | 70:30 MeOH:H₂O | 48 mL/g | 0% | — | — |

Resolution of d,l-threo α-piperid-2-ylphenylacetamide

| Resolving Agent (1.0 equiv.) | Solvent(s) | Solvent Amt. (per g. amide) | Yield | $[\alpha]_D$ | % ee |
|---|---|---|---|---|---|
| (1S)-(+)-10-camphor sulphonic acid | MeOH | 48 mL/g | 0% | — | — |
| (1S)-(+)-10-camphor sulphonic acid | EtOH | 48 mL/g | 56% | 0° | 0.0% |
| (−)-dibenzoyl-L-tartaric acid | MeOH | 48 mL/g | 0% | — | — |
| (−)-dibenzoyl-L-tartaric acid | EtOH | 48 mL/g | 0% | — | — |
| (−)-dibenzoyl-L-tartaric acid | EtOH | 10 mL/g | 0% | — | — |
| (−)-dibenzoyl-L-tartaric acid | EtOH:EtOAc | 20 mL/g | 0% | — | — |
| (−)-dibenzoyl-L-tartaric acid | H₂O:MeOH (2:1) | 30 mL/g | 100% | 0° | 0.0% |
| L-(−)-malic acid | MeOH | 48 mL/g | 0% | — | — |
| L-(−)-malic acid | EtOH | 48 mL/g | 112% | −0.3° | 0.0% |
| (S)-(+)-mandelic acid | MeOH | 48 mL/g | 0% | — | — |
| (S)-(+)-mandelic acid | EtOH | 48 mL/g | 0% | — | — |
| (S)-(+)-mandelic acid | EtOH | 10 mL/g | 0% | — | — |
| (S)-(+)-mandelic acid | EtOH:EtOAc (1:1) | 20 mL/g | 0% | — | — |
| (S)-(+)-mandelic acid | H₂O | 20 mL/g | 60% | 0° | 0.0% |

*4.0 g sample employed
**0.5 g (crude) samples employed.

EXAMPLE 3 d-Threo and l-Threo α-Piperid-2-ylphenylacetamide

A mixture of 20.0 g (92 mmol) of l-erythro α-piperid-2-ylphenylacetamide and 20 g (179 mmol) of potassium tert-butoxide in 500 mL of toluene was stirred at 70° C. for 15 hours. The reaction mixture was cooled to ambient temperature, extracted with 140 mL of 1.25M hydrochloric acid, and once with 50 mL of water. The toluene solution was concentrated to 200 mL and the crystalline d-threo amide was filtered to give 14.37 g of the product. $[\alpha]_D$ ±65.1°, (60% ethanol/water, c =1.0).

The foregoing procedure was repeated modifying the reagents and conditions as indicated below:

| Amide | Base | Solvent | Temp. | Time | Result |
|---|---|---|---|---|---|
| 2.3 mmol | 1 mL 6M KOH | Water | reflux | 6 h | SM consumed |
| 0.69 mmol | 0.88 mmol KO$^t$Bu | THF | rm. temp. | 18 h | SM:Prod = 2.5:97.5 |
| 0.69 mmol | 0.09 mmol KO$^t$Bu | THF | rm. temp | 20 h | SM:Prod = 44.56 |
| 50 mmol | 50 mmol KO$^t$Bu | THF | rm. temp | 20 h | SM:Prod = 15:82 |
| 10 mmol | 10 mmol KO$^t$Bu | Toluene | rm. temp | 5 h | SM:Prod = 12.88 |
| 172 mmol | 172 mmol KO$^t$Bu | THF | rm. temp | 4 h | SM:Prod = 16.79 |
| 5 mmol | 11 mmol KO$^t$Bu | THF | rm. temp | 16 h | SM:Prod = 8:92 |
| 2.5 mmol | 5 mmol KO$^t$Bu | Toluene | rm. temp | 16 h | SM:Prod = 4:96 |

Using d-erythro α-piperid-2-ylphenylacetamide, l-threo α-piperid-2-ylphenylacetamide, $[\alpha]_D = -65.5°$, (60% ethanol/water, c =1.0) is obtained in a similar manner.

EXAMPLE 4 d-Threo and l-Threo Methyl α-Piperid-2-ylphenylacetate Hydrochloride

A mixture of 27.83 g (128 mmol) of d-threo α-piperid-2-ylphenylacetamide and 33.4 mL of concentrated sulfuric acid in 300 mL of methanol was heated at reflux for 60 hours. The reaction mixture was cooled to ambient temperature, and concentrated in vacuo. The residue was added to 300 g of crushed ice and the pH was adjusted to 13 with 10 M sodium hydroxide. The mixture was extracted twice with 200 mL of ether and these extracts were dried over magnesium sulfate. Hydrogen chloride gas was passed through the solution and the solid was collected by filtration under suction and washed with ether to give 33.07 g of product which was recrystallized from methanol to give 26.2 g of d-threo methyl α-piperid-2-ylphenylacetate hydrochloride as a white solid. $[\alpha]_D = +85.40°$, (methanol, c=1.0).

The same procedure employing the l-threo amide yields l-threo methyl α-piperid-2-ylphenylacetate hydrochloride. $[\alpha]_D = -83.60$, (methanol, c=1.0).

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A process for preparing d-threo piperidines comprising the steps of:

reacting a pyridine having formula I:

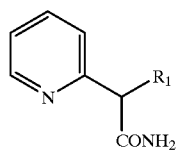

I wherein $R_1$ is aryl having about 6 to about 28 carbon atoms with hydrogen in an alkanoic acid having 1 to about 10 carbon atoms and in the presence of a catalyst to provide a mixture of threo and erythro piperidine stereoisomers having formulas IIa–d:

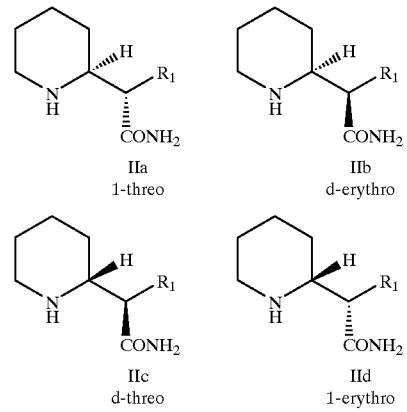

IIa
l-threo

IIb
d-erythro

IIc
d-threo

IId
l-erythro adding an alkyl alkanoate having 2 to about 20 carbon atoms to said mixture, thereby precipitating alkanoate salts of said erythro stereoisomers preferentially with respect to alkanoate salts of said threo stereoisomers;

reacting said erythro alkanoate salts with aqueous base to form said erythro stereoisomers;

reacting said erythro stereoisomers with an acid resolving agent in an alkyl alcohol having 1 to about 5 carbon atoms, thereby forming acid salts of said l-erythro stereoisomers preferentially with respect to said d-erythro stereoisomers;

reacting said l-erythro acid salts with aqueous base to form said l-erythro piperidine; and reacting said l-erythro piperidine with an alkali metal alkoxide having one to about 10 carbon atoms in organic solvent, thereby forming said d-threo piperidine.

2. The process of claim 1 wherein $R_1$ phenyl.

3. The process of claim 1 wherein said catalyst contains platinum.

4. The process of claim 1 wherein said alkyl alkanoate is ethyl acetate.

5. The process of claim 1 wherein said resolving agent is L-(+)- or D-(−)- tartaric acid.

6. The process of claim 1 wherein said alcohol is absolute methanol.

7. The process of claim 1 wherein said aqueous base is potassium hydroxide.

8. The process of claim 1 wherein said alkali metal alkoxide is potassium tert-butoxide.

9. The process of claim 1 wherein said organic solvent is an aromatic hydrocarbon.

10. The process of claim 1 further comprising separating said erythro alkanoate salts from said threo alkanoate salts.

11. The process of claim 1 further comprising separating said l-erythro amide acid salts from said d-erythro amide acid salts.

12. A process for preparing erythro piperidines, comprising the steps of:

reacting a pyridine having formula I:

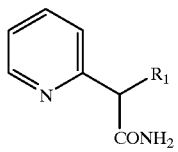

I wherein $R_1$ is aryl having about 6 to about 28 carbon atoms with hydrogen in an alkanoic acid having 1 to about 10 carbon atoms in the presence of a catalyst to provide a mixture of threo and erythro piperidine stereoisomers having formulas IIa–d:

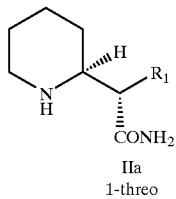
IIa
l-threo

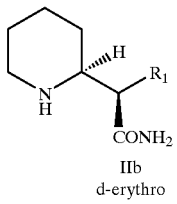
IIb
d-erythro

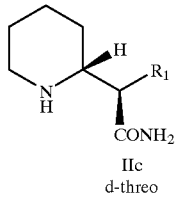
IIc
d-threo

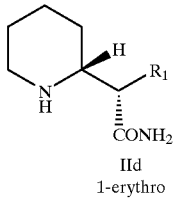
IId
l-erythro adding an alkyl alkanoate having 2 to about 20 carbon atoms to said mixture, thereby precipitating said erythro diastereomers preferentially with respect to said threo diastereomers.

13. A process for preparing l-erythro piperidine salts, comprising reacting a mixture of d-erythro and l-erythro piperidine stereoisomers having formulas IIb and IId:

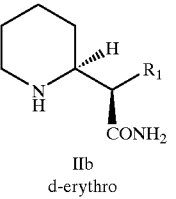
IIb
d-erythro

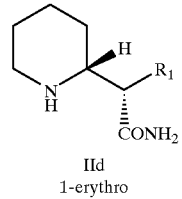
IId
l-erythro wherein $R_1$ is aryl having about 6 to about 28 carbon atoms with an acid resolving agent in absolute methanol, thereby forming acid salts of said l-erythro stereoisomer preferentially with respect to said d-erythro stereoisomer.

14. A process for preparing d-threo piperidines having formula IIc:

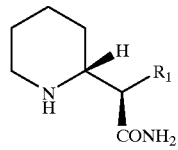

IIc
d-threo wherein $R_1$ is aryl having about 6 to about 28 carbon atoms comprising reacting l-erythro piperidine having formula IId:

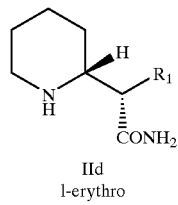

IId
l-erythro with alkali metal tert-butoxide in an organic solvent, thereby forming said d-threo piperidine.

15. The process of claim 12 wherein $R_1$ phenyl.

16. The process of claim 12 wherein said catalyst contains platinum.

17. The process of claim 12 wherein said alkyl alkanoate is ethyl acetate.

18. The process of claim 12 further comprising separating said erythro alkanoate salts from said threo alkanoate salts.

19. The process of claim 13 wherein $R_1$ phenyl.

20. The process of claim 13 wherein said resolving agent is L-(+)- or D(−)-tartaric acid.

21. The process of claim 13 further comprising separating said l-erythro amide acid salts from said d-erythro amide acid salts.

22. The process of claim 14 wherein $R_1$ phenyl.

23. The process of claim 14 wherein said organic solvent is an aromatic hydrocarbon.

* * * * *